(12) United States Patent
Otto et al.

(10) Patent No.: US 10,455,399 B2
(45) Date of Patent: Oct. 22, 2019

(54) PORTABLE MODULAR CRISIS COMMUNICATION SYSTEM

(71) Applicant: Enforcement Technology Group Inc., Milwaukee, WI (US)

(72) Inventors: Kevin L Otto, Milwaukee, WI (US); Nelson Flores, Milwaukee, WI (US); John A. Crockett, Milwaukee, WI (US)

(73) Assignee: ENFORCEMENT TECHNOLOGY GROUP INC., Milwaukee, WI (US)

( * ) Notice: Subject to any disclaimer, the term of this patent is extended or adjusted under 35 U.S.C. 154(b) by 0 days.

(21) Appl. No.: 16/207,074

(22) Filed: Nov. 30, 2018

(65) Prior Publication Data

US 2019/0166479 A1     May 30, 2019

Related U.S. Application Data

(60) Provisional application No. 62/592,749, filed on Nov. 30, 2017.

(51) Int. Cl.
| | |
|---|---|
| *H04W 4/90* | (2018.01) |
| *H04W 16/20* | (2009.01) |
| *H04W 88/08* | (2009.01) |
| *A61B 5/00* | (2006.01) |
| *A61B 5/1172* | (2016.01) |
| *A61B 5/08* | (2006.01) |
| *A61B 5/024* | (2006.01) |
| *A61B 5/16* | (2006.01) |
| *H04N 7/18* | (2006.01) |

(52) U.S. Cl.
CPC ............ *H04W 4/90* (2018.02); *A61B 5/0022* (2013.01); *A61B 5/024* (2013.01); *A61B 5/082* (2013.01); *A61B 5/1172* (2013.01); *A61B 5/165* (2013.01); *A61B 5/4803* (2013.01); *A61B 5/747* (2013.01); *H04W 16/20* (2013.01); *H04N 7/18* (2013.01); *H04W 88/085* (2013.01)

(58) Field of Classification Search
CPC ..... H04W 4/90; H04W 16/20; H04W 88/085; A61B 5/0022; A61B 5/024; A61B 5/082; A61B 5/1172; A61B 5/165; A61B 5/4803; A61B 5/747; H04N 7/18
See application file for complete search history.

(56) References Cited

U.S. PATENT DOCUMENTS

| | | | | |
|---|---|---|---|---|
| 5,794,127 | A * | 8/1998 | Lansang | H04R 1/1041 340/12.5 |
| 6,091,956 | A * | 7/2000 | Hollenberg | G06Q 30/02 455/456.5 |
| 9,137,352 | B2 | 9/2015 | Otto | |

(Continued)

*Primary Examiner* — Dominic E Rego

(57) ABSTRACT

A portable modular crisis communication system has a portable network operating center (NOC) unit and a deployable communications unit. The NOC and the deployable communications unit are communicably coupled through a network established by one or more portable networking antennas, and each have communication devices so that a NOC operator can communicate over the network with a subject through the deployable communications unit. The deployable communications unit may enable various features, such as covert surveillance, voice stress analysis, chemical threat detection, fingerprint reading, heartbeat monitoring, and radio disruption, among others.

14 Claims, 2 Drawing Sheets

(56) References Cited

U.S. PATENT DOCUMENTS

| | | | |
|---|---|---|---|
| 9,749,084 B2 | 7/2017 | Otto | |
| 9,953,210 B1* | 4/2018 | Rozploch | G06K 9/00228 |
| 10,091,662 B1* | 10/2018 | Bendlin | H04W 24/02 |
| 2002/0129000 A1* | 9/2002 | Pillai | H04L 29/06 |
| 2003/0092393 A1* | 5/2003 | Tokhtuev | G01N 1/14 |
| | | | 455/67.11 |
| 2005/0014499 A1* | 1/2005 | Knoblach | B64B 1/40 |
| | | | 455/431 |
| 2007/0061862 A1* | 3/2007 | Berger | H04N 7/163 |
| | | | 725/139 |
| 2008/0178790 A1* | 7/2008 | Hatfield | G08B 5/002 |
| | | | 116/209 |
| 2009/0097462 A1* | 4/2009 | Ganley | H04B 7/18584 |
| | | | 370/338 |
| 2009/0298461 A1* | 12/2009 | O'Reilly | H04M 1/72572 |
| | | | 455/404.2 |
| 2010/0195631 A1* | 8/2010 | Batta | H04W 24/04 |
| | | | 370/338 |
| 2010/0290388 A1* | 11/2010 | Srivastava | H04N 21/4104 |
| | | | 370/328 |
| 2012/0005578 A1* | 1/2012 | Hawkins | G06F 3/0488 |
| | | | 715/702 |
| 2013/0149990 A1 | 6/2013 | Otto | |
| 2013/0279090 A1* | 10/2013 | Brandt | H05K 7/00 |
| | | | 361/679.01 |
| 2015/0306493 A1* | 10/2015 | Hart | F41H 1/02 |
| | | | 340/323 R |
| 2016/0183109 A1* | 6/2016 | Kiesekamp | H04L 41/0609 |
| | | | 370/252 |
| 2017/0353346 A1* | 12/2017 | Pfeffer | H04L 41/065 |
| 2017/0372143 A1* | 12/2017 | Barcus | G06F 7/10 |

* cited by examiner

PORTABLE MODULAR CRISIS COMMUNICATION SYSTEM

The current application claims a priority to the U.S. Provisional Patent application Ser. No. 62/592,749 filed on Nov. 30, 2017.

FIELD OF THE INVENTION

The present invention relates generally to communication devices. More particularly, the present invention relates to a modular, deployable audio/video/data communication system designed primarily to support emergency or critical incident response communications.

BACKGROUND OF THE INVENTION

The present invention is a modular and expandable audio/video/data providing emergency communications, data gathering and networking, designed predominantly to meet the demands of law enforcement, military and like agencies seeking wireless tools to support emergency/critical incident response communications and covert audio/video intelligence gathering, and other uses.

While there are many different types emergency/critical incident response tools in use today and some work reasonably well, all of them have shortcomings because of inherent design limitations and/or failure to incorporate the entire feature set of audio/video/data networking of the present invention within a single system.

Additional advantages of the invention will be set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention will become apparent from consideration of the following detailed description given with reference to the accompanying drawings, which specify and show preferred embodiments of the present invention.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

The present invention is a modular and expandable audio/video/data system providing emergency communications, data gathering and networking, designed predominantly to meet the demands of law enforcement, military and like agencies seeking wireless tools to support emergency/critical incident response communications and covert audio/video intelligence gathering, and other uses. The present invention is designed for use in situations where wireless communication with an individual is desired in a crisis or emergency situation, such as, but not limited to, a hostage negotiation or other crisis. The preferred embodiment of the present invention further comprises a proprietary operating system and operational software in order to fulfill the functionality of the various physical components of the present invention.

Figure 1:
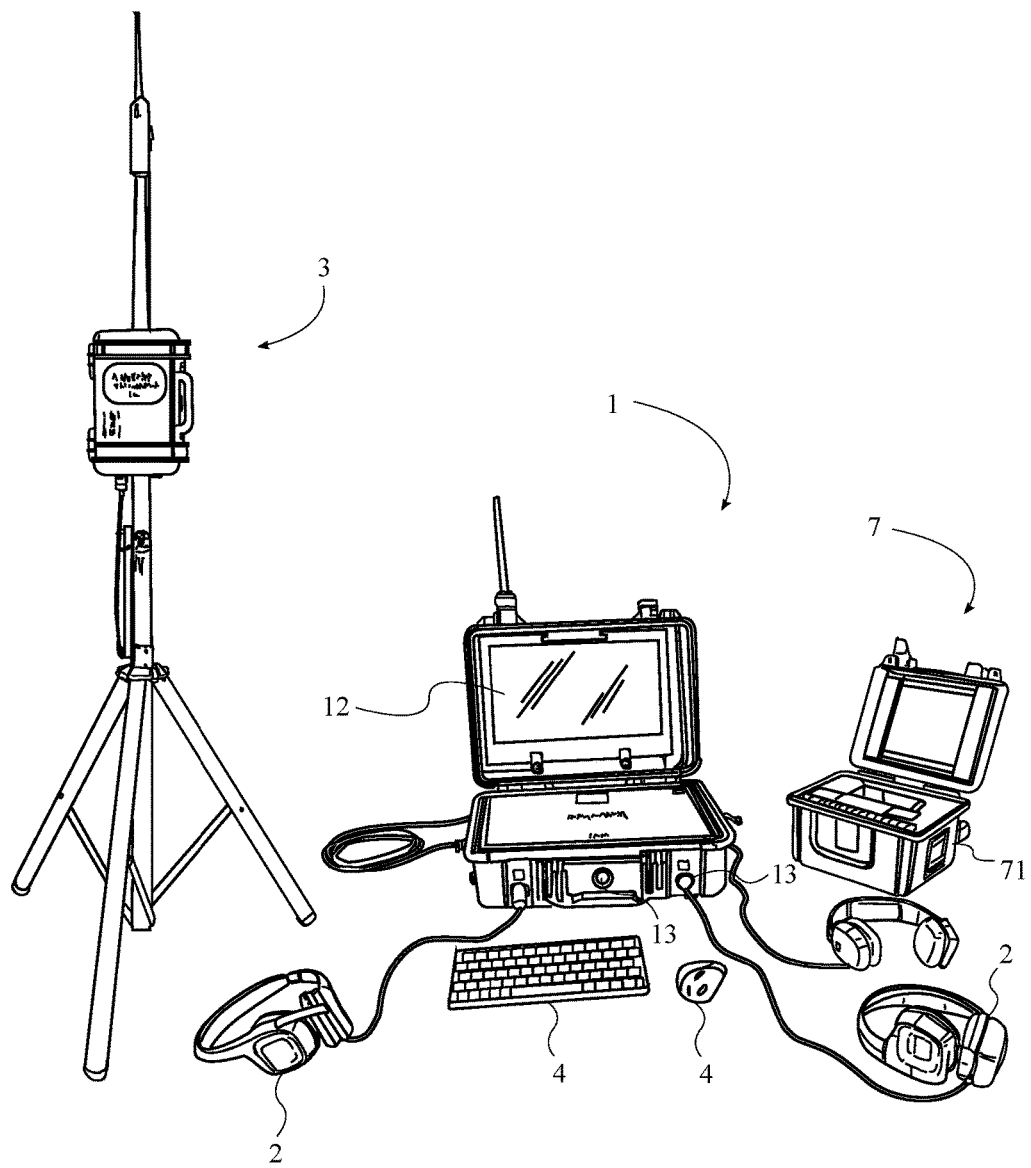
FIG. 1 is an overview illustration of the components of the present invention.
Figure 2:
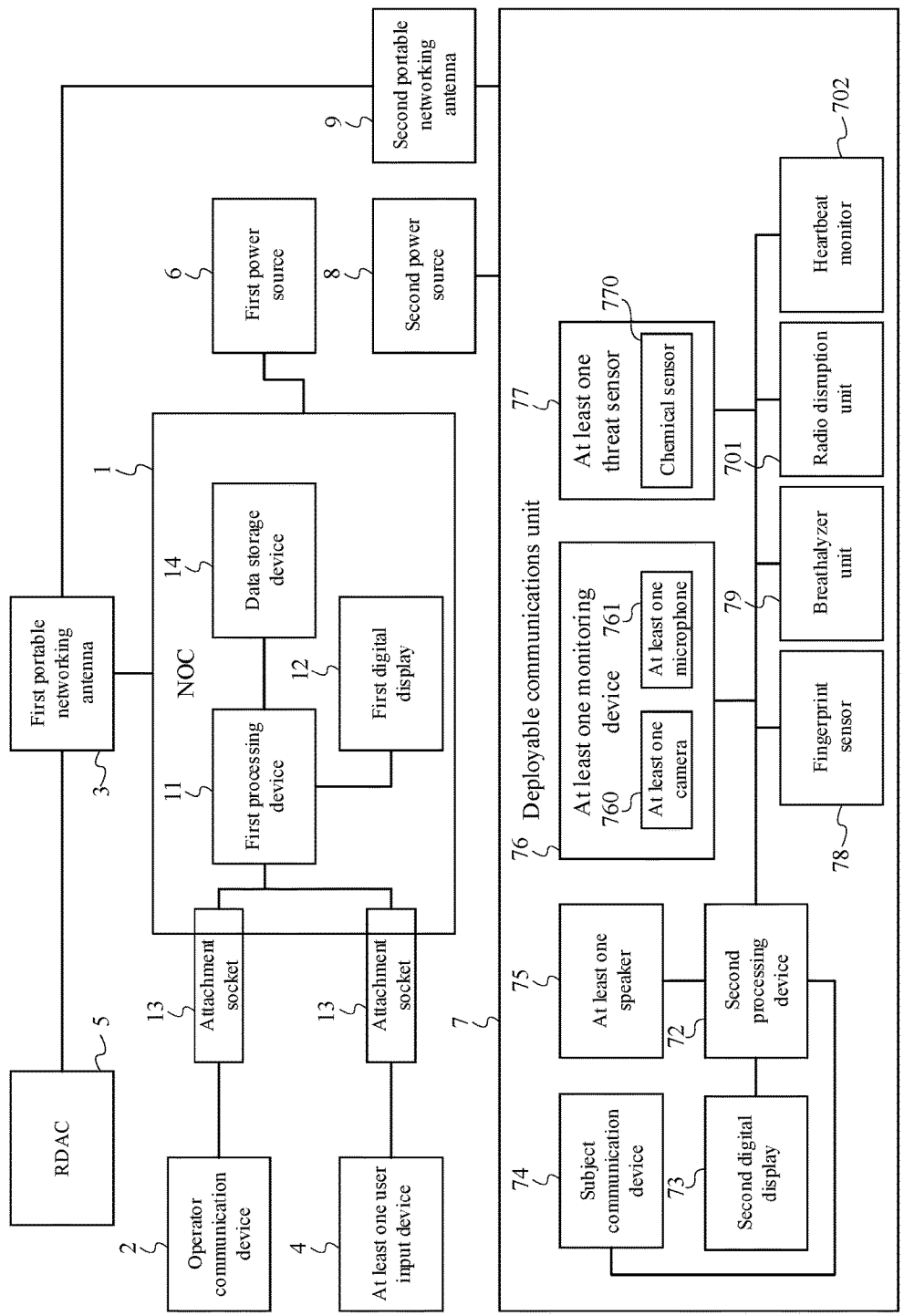
FIG. 2 is a general diagram of electrical, electronic and communicative connections in the present invention.

Referring to FIGS. 1-2, in general, the present invention comprises a network operating center (NOC) 1, an operator communication device 2, a first portable networking antenna 3, at least one user input device 4, at least one remote data access center (RDAC) 5, a first power source 6, a deployable communications unit 7, a second power source 8, and a second portable networking antenna 9.

The NOC 1 is a portable observation and communication module designed to be a primary operating station for an operator such as emergency, military or other personnel at a crisis site. The operator utilizes the NOC 1 to communicate with the deployable communications unit 7, which may be deployed to a location accessible by an individual involved in the crisis situation, such as a fugitive or other individual secluded or inhibited from face-to-face communication with the emergency personnel. The NOC 1 comprises a first processing device 11 and a first digital display 12. The operator communication device 2, the first portable networking antenna 3, the at least one user input device 4, and the first digital display 12 are electronically connected to the first processing device 11 of the NOC 1. The first power source 6 is electrically connected to the NOC 1. Preferably, the operator communication device 2 is a headset through which the operator can communicate with the deployable communications unit 7. Furthermore, the at least one user input device 4 may comprise, but is not limited to, a keyboard, a mouse, a handheld controller, or another user input device 4.

In the preferred embodiment, the NOC 1 further comprises a data storage device 14. The data storage device 14 is electronically connected to the first processing device 11. The first processing device 11 is configured to receive at least one data stream from the deployable communications unit 7 and store the at least one data stream on the data storage device 14.

Each of the at least one RDAC 5 is communicably coupled with the NOC 1 through the first portable networking antenna 3. In the context of the present invention, a RDAC 5 is a station or unit that allows additional personnel to monitor any audio, video, or other data captured by the deployable communications unit 7, similar to the NOC 1, but primarily in an observational capacity. Each of the at least one RDAC 5 may be communicably coupled with the NOC 1 through the first portable networking antenna 3, or another means of electronic communication such as a cellular or satellite network. Thus, a user may interact with the RDAC 5 in order to monitor a crisis situation in real time even from a location remote to the crisis location.

In the preferred embodiment of the present invention, the NOC 1 comprises a plurality of attachment sockets 13, through which a variety of peripheral devices and accessories may be connected to the system. In some embodiments, the operator communication device 2, the portable networking antenna, and the at least one user input device 4 may each be electronically connected to the NOC 1 through the plurality of attachment sockets 13. Each of the plurality of attachment sockets 13 may receive a compatible adapter connected to a peripheral device, through which the peripheral device is electrically or electronically connected to the NOC 1. In this way, the present invention is expandable and modular and may be configured in various ways with various peripheral components to fit various different situational requirements.

As previously mentioned, the deployable communications unit 7 is a device intended to be deployed into the midst of a crisis situation in order to communicate with an individual involved in the crisis situation. For example, the deployable communications unit 7 may be thrown by an emergency personnel into the vicinity of the individual, such as a building or room where a fugitive has taken refuge, or into a cave, ravine or other location into which an individual has fallen or become trapped. Preferably, the deployable communications unit 7 is made from durable materials and is constructed to withstand minor or impacts, such as those resulting from being thrown or dropped from a substantial height.

In the preferred embodiment of the present invention, the deployable communications unit 7 comprises a case 71, a second processing device 72, a second digital display 73, a subject communication device 74, at least one speaker 75, and at least one monitoring device 76. The second power source 8 is electrically connected to the deployable communications unit 7, and thereby to any components of the deployable communications unit 7 requiring electrical power, and the second portable networking antenna 9 is electronically connected to the deployable communications unit 7, enabling wireless communication with the NOC 1.

In the preferred embodiment of the present invention, the second digital display 73, the subject communication device 74, the at least one speaker 75, and the at least one monitoring device 76 are integrated into, connected to or attached to the case 71 in any desirable manner. The second digital display 73, the subject communication device 74, the at least one speaker 75, and the at least one monitoring device 76 are furthermore electronically connected to the processing device of the deployable communications unit 7.

The first portable networking antenna 3 and the second portable networking antenna 9 are configured to wirelessly communicate with each other through a network connection, enabling communication and data transfer between the NOC 1 and the deployable communications unit 7. The first processing device 11 is configured to send and receive a plurality of communication signals to and from the deployable communications unit 7 through the network connection.

In the preferred embodiment, the first power source 6 and the second power source 8 are each embodied as a rechargeable, replaceable battery pack. In the preferred embodiment, the first battery pack is removably connected to the NOC 1, and the second battery pack is removably connected to the case 71 of the deployable communications unit 7. However, it is contemplated that in various embodiments, any desired means to provide electrical power to the NOC 1 and the deployable communications unit 7 may be employed. For example, the NOC 1 may be directly connected to an external power source.

The at least one monitoring device 76 of the deployable communications unit 7 is intended to provide an operator at the NOC 1 with covert surveillance capabilities to supplement the direct communication capability provided by the subject communication device 74. Therefore, the at least one monitoring device 76 should be integrated into the case 71 in a manner which conceals the at least one monitoring device 76 or inhibits the subject from recognizing it. In the preferred embodiment, the at least one monitoring device 76 comprises at least one camera 760, and the second processing device 72 of the deployable communications unit 7 is configured to capture a video feed through the at least one camera 760 and send the video feed over the network to the NOC 1, wherein the NOC 1 is configured to display the video feed. Thus, the operator of the NOC 1 is able to visually monitor the surroundings of the deployable communications device at any given moment. Furthermore, in the preferred embodiment the at least one monitoring device 76 additionally comprises at least one microphone 761 configured to capture an audio feed, and the second processing device 72 is further configured to send the audio feed to the NOC 1 over the network. Thus, the NOC 1 operator is further able to monitor any sounds produced in the vicinity of the deployable communications unit 7.

In various embodiments, the deployable communications unit 7 may be configured with various components and features that enable various functionalities. In some embodiments, the deployable communications device may further comprise at least one threat sensor 77 electronically connected to the second processing device 72. The at least one threat sensor 77 may be a chemical sensor 770 in some embodiments, or the at least one threat sensor 77 may be one of a variety of threat sensors in different embodiments.

In the preferred embodiment, in conjunction with the at least one microphone 761, the first processing device 11 of the NOC 1 is configured to execute a voice stress analysis on the audio feed.

In some embodiments, the deployable communications device may further comprise a fingerprint sensor 78, with the fingerprint sensor 78 being integrated into or connected to the case 71 and electronically connected to the second processing device 72. The fingerprint sensor 78 allows the subject to input their fingerprint into the deployable communications unit 7, which transmits the fingerprint to the NOC 1 for analysis.

In some embodiments, the deployable communications device may further comprise a breathalyzer unit 79, with the breathalyzer unit 79 being integrated into or connected to the case 71 and electronically connected to the second processing device 72. The subject may blow into the breathalyzer unit 79, which then analyzes the subject's breath to acquire a blood alcohol percentage reading, and the blood alcohol percentage reading may then be transmitted to the NOC 1 over the network for analysis.

In some embodiments, the deployable communications device may further comprise a radio disruption unit 701, with the radio disruption unit 701 being integrated into or connected to the case 71 and electronically connected to the second processing device 72. The radio disruption unit 701 allows the NOC 1 operator to send a radio disruption signal from the NOC 1 to the deployable communications unit 7 over the network. The radio disruption signal is then received by the second processing device 72, which then activates the radio disruption unit 701, allowing the NOC 1 operator to disable any radio transmissions in the vicinity of the deployable communications unit 7.

In some embodiments, the deployable communications device may further comprise a heartbeat monitor 702, with the heartbeat monitor 702 unit being integrated into or connected to the case 71 and electronically connected to the second processing device 72. The heartbeat monitor 702 allows the NOC 1 operator to receive a reading of the subject heartbeat, provided the subject cooperates and interacts appropriately with the heartbeat monitor 702.

Preferably, the present invention utilizes a proprietary operating system and software in order to facilitate the execution of the desired functions of the present invention, including a graphical user interface (GUI) purpose-built for interacting with the present invention appropriately. The software of the present invention preferably enables many desired features of the present invention, including, but not limited to: two-way audio, video, and text communication, voice stress analysis, heartbeat monitor and analysis, chemical threat detection, sonar, fingerprint identification, breathalyzer function and analysis, sonic nausea, two-dimensional video layout/design-video enhancement, data distribution, radio frequency (RF) disruption, and radio defined software/technology. Furthermore, a portal may be provided in the system for use or integration with other software or applications, facilitating connectivity, data distribution, and any other relevant desired functions.

The following is a supplemental description of the present invention in accordance with some embodiments, and is not intended to be limiting, and is rather intended to further exemplify the spirit of the present invention.

The present invention is an audio/video/data networking system composed of, but not limited to:

A portable Network Operating Center (NOC) inclusive of a proprietary operating system with Networking Antenna placement and repeaters; a Wireless Video Phone Handset with instant messaging/texting abilities; the system is modular, accommodating various needs; the system is capable of wireless, semi-wireless and wired operations, comprising, but not limited to an Audio and Video observation module/Throw Phone housing ("deployable communications unit" as referred to above) providing a plurality of audio and video data inclusive of live and streaming viewing/monitoring, A deployment case with Portable Networking Antenna and External/Rechargeable Power Pack; and a single or multiple Remote Data Access Centers (RDACs).

Basic Set-Up & Operations:
1. Connect the following components to the system's Network Operating Center (NOC):
   a. Communication Headset ("operator communication device" as referred to above)
   b. Portable Networking Antenna
   c. A single or multiple Remote Data Access Centers (RDACs)
   d. A Keyboard (one of the "at least one user input device" as referred to above)
   e. A Mouse (one of the "at least one user input device" as referred to above)
2. Connect the NOC to an external power supply or custom rechargeable battery pack and power on.
3. Transport the Semi-Wireless Video Throw Phone/Deployment Case (containing the Wireless Video Phone Handset) with Portable Networking Antenna and External Rechargeable Power Pack within the vicinity of the crisis environment.
4. Connect the cable attached to the Semi-Wireless Video Throw Phone/Deployment Case to the Portable Networking Antenna and power on the External/Rechargeable Power Pack.
5. Deploy the Semi-Wireless Video Throw Phone/Deployment Case (containing the Wireless Video Phone Handset) inside of the crisis environment.

After the basic set-up and operations have been performed, the law enforcement operator (i.e. Crisis Negotiator) wearing the Communication Headset at the NOC may establish 2-way, full-duplex verbal communications with an individual/subject located within the crisis environment over the Wireless Video Phone Handset and/or the telephone handset contained within the Semi-Wireless Video Throw Phone/Deployment Case.

Notably, the Semi-Wireless Video Throw Phone/Deployment Case preferably features a clear, see-through lid. This allows for the subject to identify the contents of the case without it having to be opened. Furthermore, the Wireless Video Phone Handset is mounted in subject a way to allow the subject to read a custom message issued by the Crisis Negotiator on the Handset's display (e.g. We want to talk with you, please pick up the phone).

If the subject is unwilling or unable to verbally communicate with the Crisis Negotiator, the Crisis Negotiator may choose to broadcast verbal commands through the Video Throw Phone Handset and/or the Semi-Wireless Video Throw Phone/Deployment Case's built-in speakers.

If the subject remains unresponsive to the Crisis Negotiator's commands or is hearing impaired, the Crisis Negotiator may choose activate the Wireless Video Throw Phone's 2-way instant messaging feature to communicate.

In addition to housing a telephone handset, the Semi-Wireless Video Throw Phone/Deployment Case also houses multiple covert color day/night cameras as well as a hidden microphone (the at least one monitoring device as referred to above). The covert video and audio data provided by these hidden cameras and microphone is streamed to a single or multiple Remote Data Access Centers (RDACs) that are connected to the NOC. This allows for additional law enforcement operators such as Tactical and/or Incident Command with the ability to access audio/video intelligence and/or monitor the communications taking place between the Crisis Negotiator and the subject from within the crisis environment at any time. Tactical and/or Incident Command personnel may also use the RDAC(s) to watch streaming video provided from the Video Throw Phone Handset's built-in front or rear facing cameras as well as listen to sounds or voice being picked up by the Handset's built-in microphone as well.

The NOC and the RDAC(s) also incorporate verbal and instant messaging communication features. This allows for law enforcement operators situated at these components to communicate with one another to better coordinate response efforts.

Other unique features of the present invention include:
Self-contained Point to Point Wireless, cellular, satellite or other RF transceiver means supplying a multitude of Connectivity options:
Expandability: The system's network platform is designed to be expandable, so it may be used (is interoperable) with current law enforcement/military audio/video surveillance technologies such as drones, robots and IP cameras as well as other proprietary surveillance technologies that are in development. As the system's audio/video/data is digital it may also be streamed to the Internet via secured servers to allow it to be monitored by individuals located throughout the world.
Audio/Video Data Recording Capability: Audio/video transmitted through the system is automatically recorded to a built-in hard drive contained within the NOC for review and/or evidentiary purposes.

Built-In Bluetooth with proprietary layout and design interface

Bluetooth® technology contained within the NOC allows the component to be wirelessly connected to a cell phone handset. Once a cell phone handset has been paired the NOC, the communications taking place between the Crisis Negotiator and the subject over the cell phone handset between are recorded and are also able to be monitored in real-time at any of RDAC(s) connected. The other major benefit of the system's built-in Bluetooth® technology is that it may be used to introduce to 3rd Party Intermediary (TPI) that is NOT located on-scene assist in the negotiations that are taking place between the Crisis Negotiator and the subject over the Wireless Video Throw Phone Handset and/or the Wireless Video Throw Phone/Deployment Case.

Proprietary Software & Graphical User Interface (GUI): The proprietary software installed within the NOC and the Wireless Video Throw Phone Handset allows for the operator to manipulate various controls and settings such as signal strength and battery power levels.

Proprietary PCB design, layout and interface

Incident Management Software/Report Writing Software

Proprietary Software & Graphical User Interface (GUI)

Although the invention has been explained in relation to its preferred embodiment, it is to be understood that many other possible modifications and variations can be made without departing from the spirit and scope of the invention as hereinafter claimed.

What is claimed is:

1. A portable modular crisis communication system comprises:
   a network operating center (NOC);
   an operator communication device;
   a first portable networking antenna;
   at least one user input device;
   at least one remote data access center (RDAC);
   a first power source;
   the first power source being electrically connected to the NOC;
   the NOC comprises a first processing device and a first digital display;
   the operator communication device, the first portable networking antenna, the at least one user input device, and the first digital display being electronically connected to the first processing device;
   each of the at least one RDAC being communicably coupled with the NOC through the first portable networking antenna;
   a deployable communications unit;
   a second power source;
   a second portable networking antenna;
   the second power source being electrically connected to the deployable communications unit;
   the second portable networking antenna being electronically connected to the deployable communications unit;
   the deployable communications unit comprises a case, a second processing device, a second digital display, a subject communication device, at least one speaker, and at least one monitoring device;
   the second digital display, the subject communication device, the at least one speaker, and the at least one monitoring device being integrated into the case;
   the second digital display, the subject communication device, the at least one speaker, and the at least one monitoring device being electronically connected to the processing device of the deployable communications unit;
   the first portable networking antenna and the second portable networking antenna being configured to wirelessly communicate with each other through a network connection; and
   the first processing device being configured to send and receive a plurality of communication signals from the deployable communications unit through the network connection.

2. The portable modular communication system as claimed in claim 1 comprises:
   the first power source being a first battery pack; and
   the first battery pack being removably connected to the NOC.

3. The portable modular communication system as claimed in claim 1 comprises:
   the second power source being a second battery pack; and
   the second battery pack being removably connected to the case of the deployable communications unit.

4. The portable modular communication system as claimed in claim 1 comprises:
   the at least one monitoring device comprises at least one camera; and
   the deployable communications unit being configured to capture a video feed through the at least one camera and send the video feed over the network to the NOC, wherein the NOC is configured to display the video feed.

5. The portable modular communication system as claimed in claim 1 comprises:
   the at least one monitoring device comprises at least one microphone;
   the at least one microphone being configured to capture an audio feed; and
   the second processing device being configured to send the audio feed to the NOC over the network.

6. The portable modular communication system as claimed in claim 5 comprises:
   the first processing device of the NOC being configured to execute a voice stress analysis on the audio feed.

7. The portable modular communication system as claimed in claim 1 comprises:
   the NOC comprises a plurality of attachment sockets; and
   the operator communication device, the portable networking antenna, and the at least one user input device being electronically connected to the NOC through the plurality of attachment sockets.

8. The portable modular communication system as claimed in claim 1 comprises:
   the NOC further comprises a data storage device;
   the data storage device being electronically connected to the first processing device; and
   the first processing device being configured to receive at least one data stream from the deployable communications unit and store the at least one data stream on the data storage device.

9. The portable modular communication system as claimed in claim 1 comprises:
   the deployable communications device further comprises at least one threat sensor; and
   the at least one threat sensor being electronically connected to the second processing device.

10. The portable modular communication system as claimed in claim 9 comprises:
    the at least one threat sensor being a chemical sensor.

11. The portable modular communication system as claimed in claim 1 comprises:
   the deployable communications device further comprises a fingerprint sensor;
   the fingerprint sensor being electronically connected to the second processing device; and
   the fingerprint sensor being integrated into the case.

12. The portable modular communication system as claimed in claim 1 comprises:
   the deployable communications device further comprises a breathalyzer unit;
   the breathalyzer unit being electronically connected to the second processing device; and
   the breathalyzer unit being integrated into the case.

13. The portable modular communication system as claimed in claim 1 comprises:
   the deployable communications device further comprises a radio disruption unit;
   the radio disruption unit being electronically connected to the second processing device; and
   the radio disruption unit being integrated into the case.

14. The portable modular communication system as claimed in claim 1 comprises:
   the deployable communications device further comprises a heartbeat monitor;
   the heartbeat monitor being electronically connected to the second processing device; and
   the heartbeat monitor being integrated into the case.

* * * * *